(12) United States Patent
Levin et al.

(10) Patent No.: US 6,605,048 B1
(45) Date of Patent: Aug. 12, 2003

(54) VACUUM DEVICE TO ASSIST IN THE DRAWING OF CAPILLARY BLOOD SAMPLES

(75) Inventors: Paul D. Levin, Santa Cruz, CA (US); John D. Harding, Ben Lomond, CA (US)

(73) Assignee: Palco Labs, Inc., Santa Cruz, CA (US)

( * ) Notice: Subject to any disclaimer, the term of this patent is extended or adjusted under 35 U.S.C. 154(b) by 0 days.

(21) Appl. No.: 09/620,207

(22) Filed: Jul. 19, 2000

Related U.S. Application Data
(60) Provisional application No. 60/205,639, filed on May 18, 2000.

(51) Int. Cl.[7] .............................. A61B 5/00; B65D 81/00
(52) U.S. Cl. ........................................................ 600/578
(58) Field of Search ............................ 600/578, 576, 600/573, 566, 567; 606/172, 182; 604/187, 227; 401/176

(56) References Cited

U.S. PATENT DOCUMENTS

| | | | |
|---|---|---|---|
| 4,664,128 A | * 5/1987 | Lee | 600/566 |
| 5,368,047 A | * 11/1994 | Suzuki et al. | 600/578 |
| 5,916,230 A | * 6/1999 | Brenneman et al. | 606/172 |
| 6,234,980 B1 | * 5/2001 | Bell | 600/578 |

* cited by examiner

*Primary Examiner*—Max F. Hindenburg
*Assistant Examiner*—Brian Szmal
(74) *Attorney, Agent, or Firm*—Bruce H. Johnsonbaugh

(57) ABSTRACT

A vacuum device is provided which assists in the drawing of blood samples from alternative puncture sites such as the forearm, abdomen or inner thigh and which may advantageously be used by diabetics. The device includes a hollow body which slidably receives a hollow plunger. A transparent cylindrical tip is attached to the lower end of the hollow body. A spring is carried inside the hollow body and hollow plunger, the lower end of the spring seating against a webbing formed in the transparent tip and the upper end seating against the upper end of the plunger. The device is actuatable by the thumb and two fingers of one hand. The plunger is depressed, the device is placed over a preexisting puncture site, and the plunger is released wherein the internal spring drives the plunger upwardly and creates a vacuum at the puncture site, allowing the user to easily see the formation of a droplet of adequate size for obtaining the necessary blood reading.

6 Claims, 14 Drawing Sheets

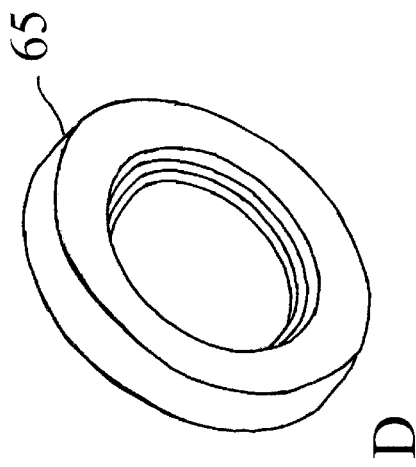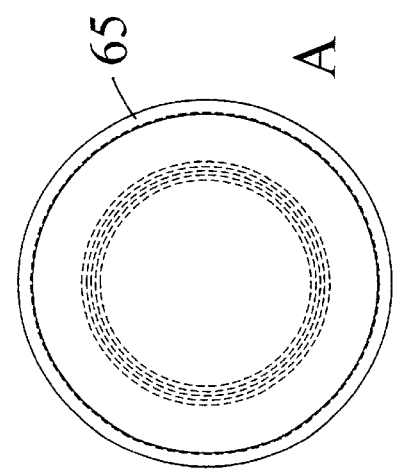
Fig. 17

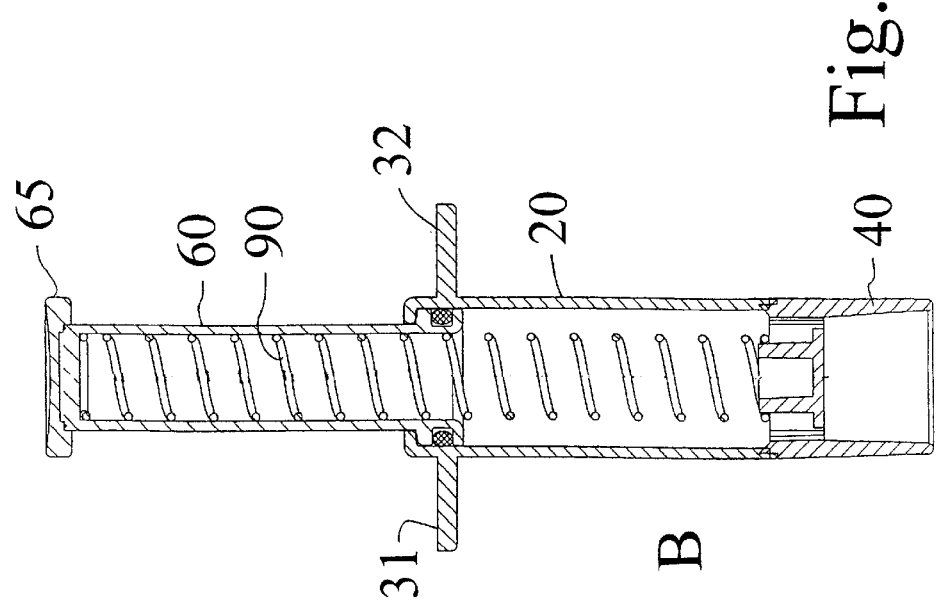
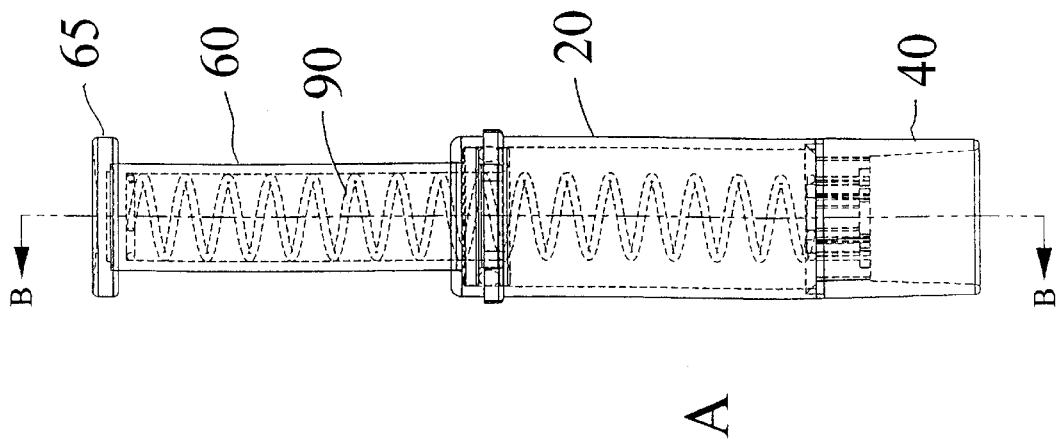
Fig. 19

VACUUM DEVICE TO ASSIST IN THE DRAWING OF CAPILLARY BLOOD SAMPLES

CROSS REFERENCE TO RELATED APPLICATION

This application claims the benefit of and priority from U.S. provisional application Ser. No. 60/205,639 dated May 18, 2000.

BACKGROUND AND SUMMARY

This application relates generally to devices used by diabetics for obtaining blood samples. More particularly, the present invention provides a simple but effective vacuum device which assists in drawing blood samples from alternative puncture sites, such as the forearm, abdomen or inner thigh.

Frequent samplings of capillary blood from the fingertip is now the standard of care in the management of diabetes. Samplings may be needed as often as 8–10 times per day for control of this common metabolic disorder. The problem of fingertip discomfort has encouraged a search for alternative sites for capillary blood sampling. The underside of the forearm, the abdomen and the inner thigh are attractive sites because of their lower number of nerve endings as compared to the fingertips. Unfortunately, these alternative sites, while having fewer sensitive nerve endings, are also less likely to bleed readily when perforated by a lancet.

This well-recognized dilemma has been approached in a number of ways by various inventors and makers of equipment for diabetics. For example, attempts have been made to design a lancet device with an internal vacuum so that, immediately after causing a skin perforation, the vacuum inside the device encourages the formation of a blood drop. Many such devices are described in the patient literature. Examples are seen in U.S. Pat. Nos. 6,027,459; 5,891,053; 5,662,127; 5,666,966; 5,368,047; 4,895,147 and 4,653,513. All of the above mentioned designs are relatively complicated and therefore difficult and expensive to produce.

A simpler approach is presented in U.S. Pat. No. 5,054,499 which describes a bendable, collapsible metal dome with a skin piercing member attached to the underside of the dome. Deformation followed by reformation of the original shape of the dome is said to form a partial vacuum over the puncture site and assist in the formation of a capillary blood sample. Disadvantages of this device are the inability to see the sample, or to repeat the flexion of the metal dome if necessary, as well as the minimal amount of vacuum which can be obtained using this type of device.

Another approach is described in several patents assigned to Mercury Diagnostics (now Amira Medical). Listed U.S. Pat. Nos. of Amira are 5,867,983; 5,951,493; 5,964,718; 5,879,311 and 6,015,392. All of these patents describe devices with so-called "stimulator rings" which, in various ways, surround the puncture site and, when forced down against the skin, urge the blood towards, and then out of, the skin incision. A disadvantage in all of the Amira devices is the inability to see whether an adequate blood drop has actually formed at the puncture site. Mechanically, the devices described in these Amira patents are cumbersome and expensive to manufacture.

The prior art includes various hand-held vacuum devices. For example, U.S. Pat. No. 5,871,456 provides a hand-held device vacuum device for correcting flat, inverted or retracted nipples. The device also includes a transparent tip. However, the device requires the use of two hands and does not use a spring to help generate a vacuum. Vacuum devices have also been proposed for the extraction of toxic venoms, pus or other body fluids from a skin puncture site. Goodrich in U.S. Pat. No. 5,387,203 teaches a tubular device with a plunger which is pulled upwards by the user to create an internal vacuum. Tissue is pulled into the device by the vacuum and lanced by an internal piercing member. A device specifically designed for venom extraction is taught by Andre Emerit in U.S. Pat. No. 4,287,819. In this two-chambered device, downward pressure on a plunger expels air from a lower chamber while creating a vacuum in an upper chamber. In the final moment of depression of the plunger, the two chambers are connected by an orifice in the hollow plunger, causing a vacuum over the skin. A device based on U.S. Pat. No. 4,287,819 is presently marketed by Sawyer Products of Long Beach, Calif. A disadvantage of the device is the suddenness of the vacuum application and the inability to vary its force. A related device is taught by Michel Emerit in U.S. Pat. No. 5,984,876. Neither Emerit device uses any kind of internal spring, therefore differing fundamentally from the present invention.

The invention to be described has advantages over prior devices in that it is small, simple to use and inexpensive to manufacture. A transparent tip allows easy viewing of the developing blood drop. The amount of vacuum force can be readily controlled by the user. If necessary, the vacuum can be recreated without removing the device from the skin or disturbing an already partially formed drop. These and other advantages will become apparent with further descriptions of the device.

DETAILED DESCRIPTION OF THE DRAWINGS

FIGS. 17A–17D are scale drawings showing the plastic injection molded plunger cap;

FIGS. 19A and 19B are frontal and sectional views showing the plunger pushed completely upward by the internal spring.

DETAILED DESCRIPTION OF THE DRAWINGS

Figure 3:
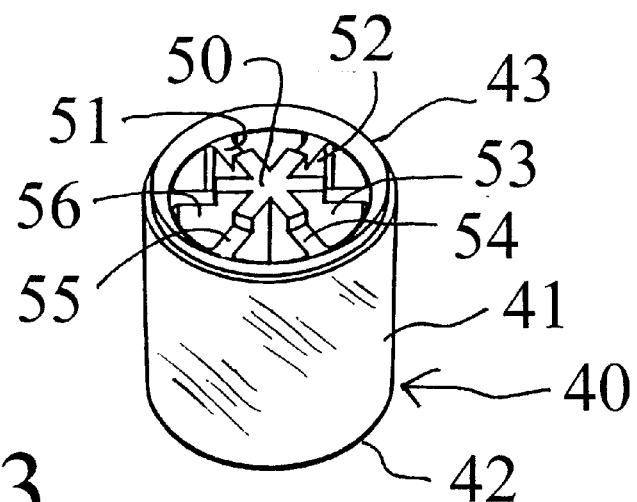
FIG. 3 is a perspective view of the transparent tip which forms a portion of a vacuum chamber when the device is activated.
Figure 4:
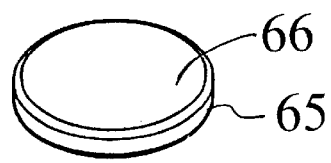
FIG. 4 is a perspective view of the plunger cap utilized with the present invention.

The drawings show the device of the present invention that assists in the drawing of capillary blood samples from alternative sites, such as the forearm, abdomen or inner thigh. The preferred embodiment is comprised of four injection molded plastic parts; an outer cylindrical body 20 with lateral finger flanges 31 and 32 (FIG. 2), a hollow plunger 60 (FIG. 5), a plunger cap 65 (FIG. 4), and a tip 40 which is transparent and which becomes a vacuum chamber when the device is activated (FIG. 3). The device also contains an inner compression spring 90 (FIG. 7) and an "O" ring 80 (FIG. 6) which fits into a circular groove near the lower end of the plunger.

Figure 8:
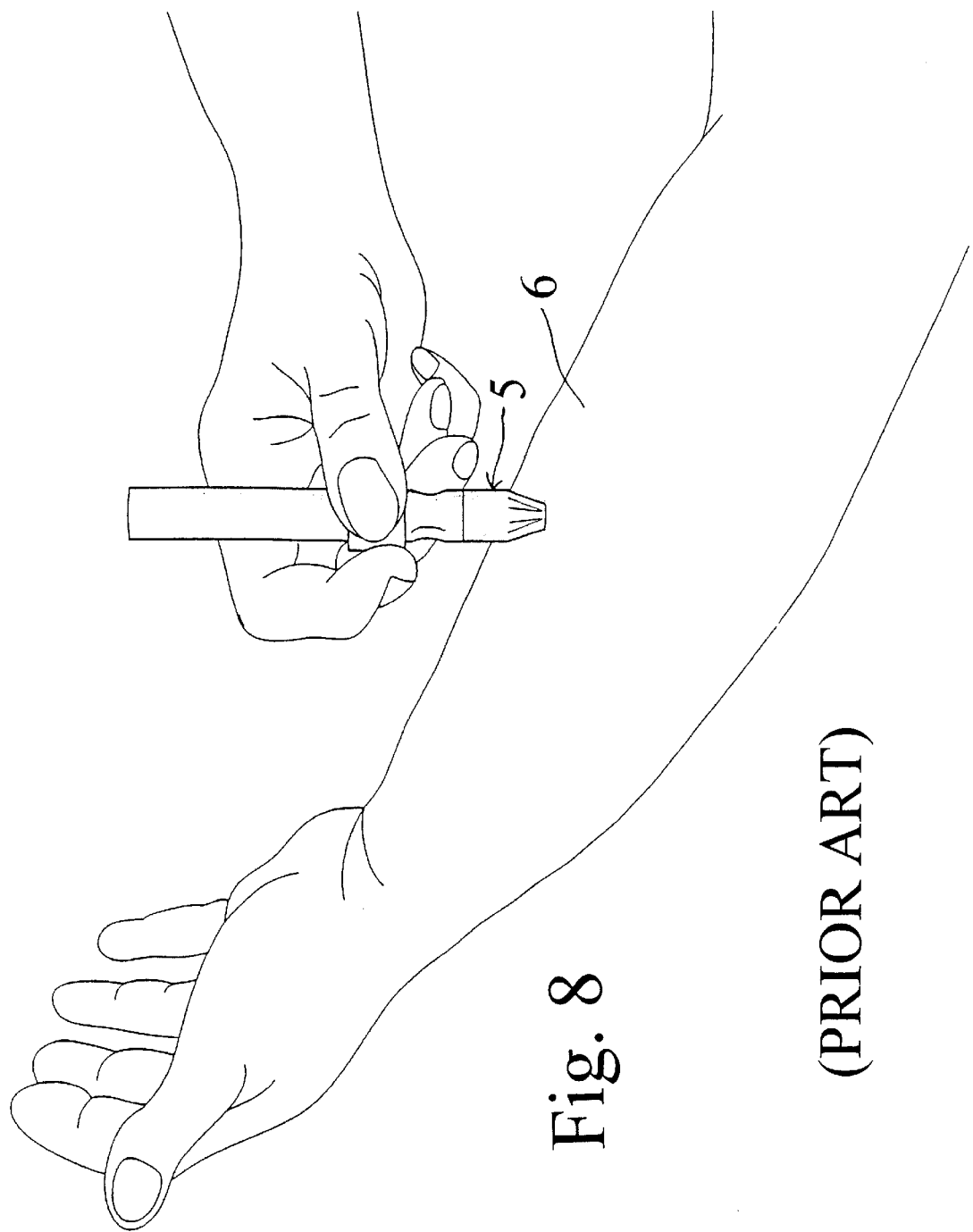
FIG. 8 shows a user utilizing a prior art lancet device to pierce the forearm skin.
Figure 10:
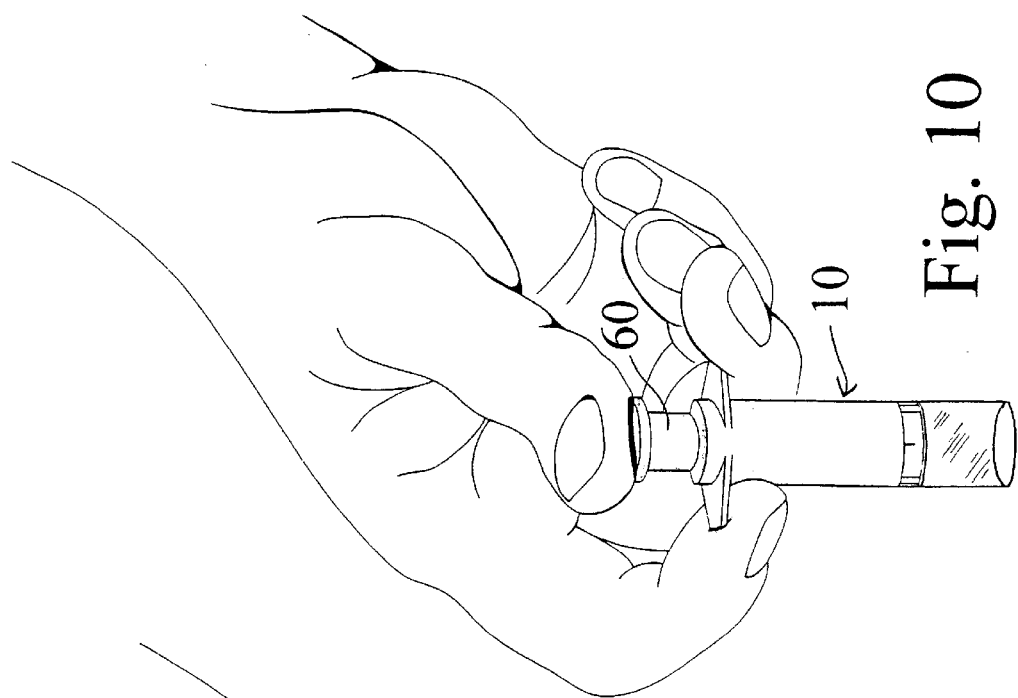
FIG. 10 is a perspective view showing the plunger in its depressed position.
Figure 9:
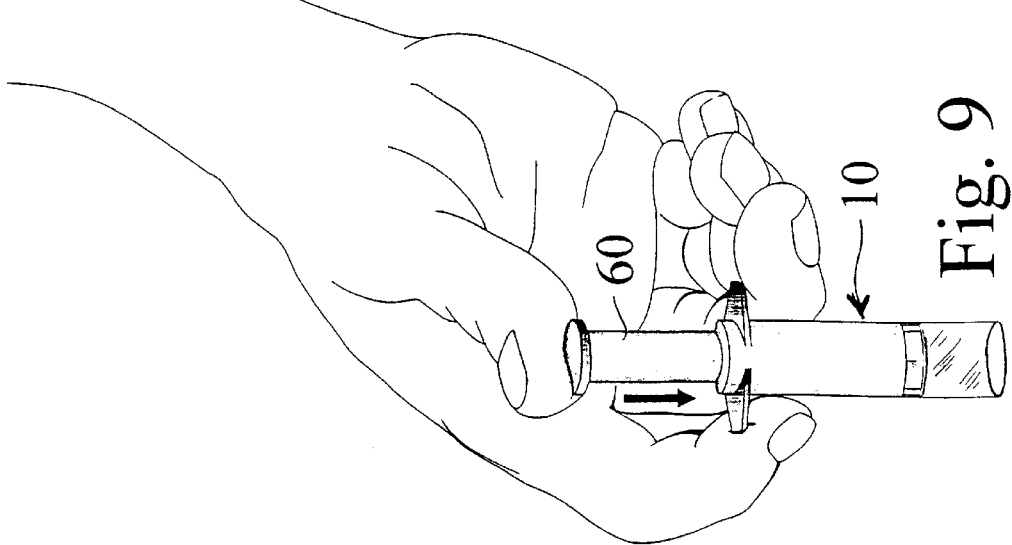
FIG. 9 is a perspective view showing a user depressing the plunger with his thumb while holding the finger flanges with two fingers.
Figure 12:
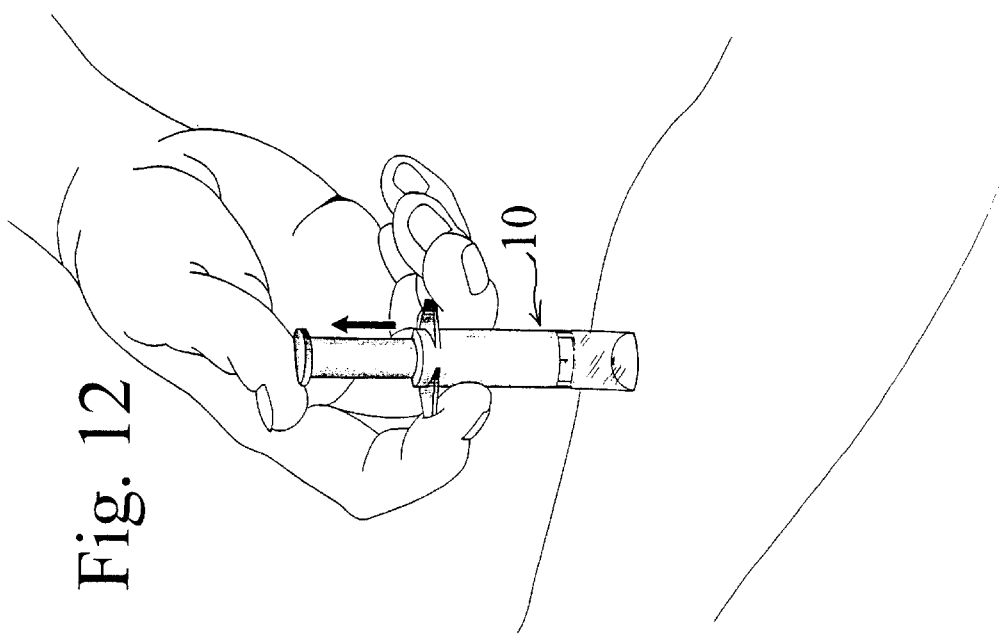
FIG. 12 shows the user allowing the plunger to be pushed upwards by the internal spring, creating a vacuum and enlarging the blood droplet at the puncture site.
Figure 11:
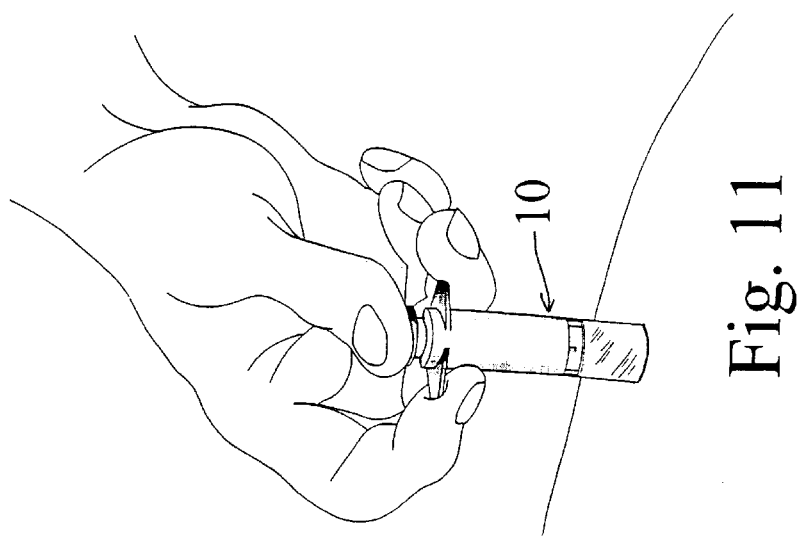
FIG. 11 shows the user placing the transparent tip of the vacuum device over the puncture site formed as shown in FIG. 8, with the plunger depressed.
Figure 13:
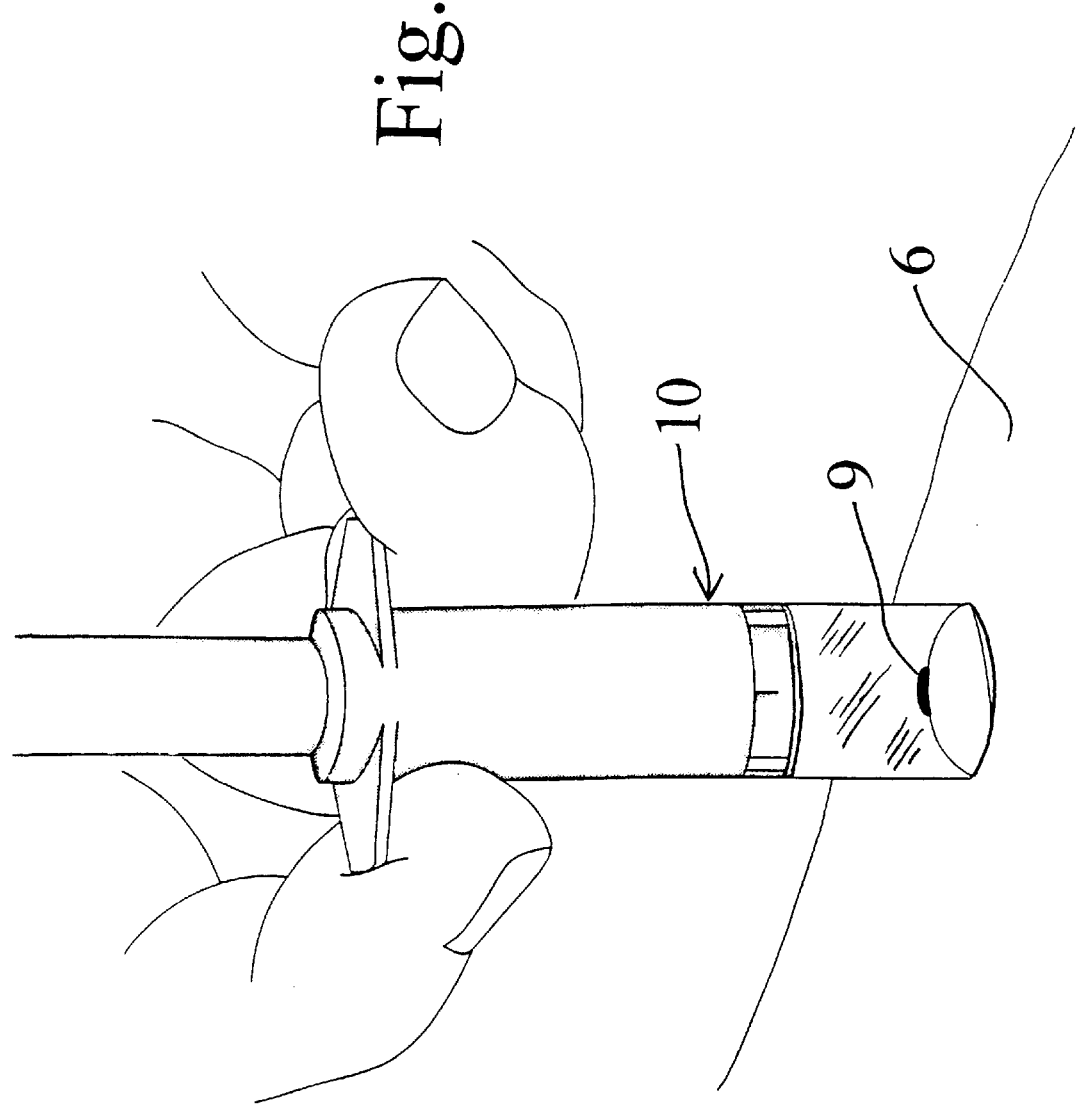
FIG. 13 shows the enlarged blood droplet underneath the transparent tip of the invention in response to the vacuum.
Figure 14:
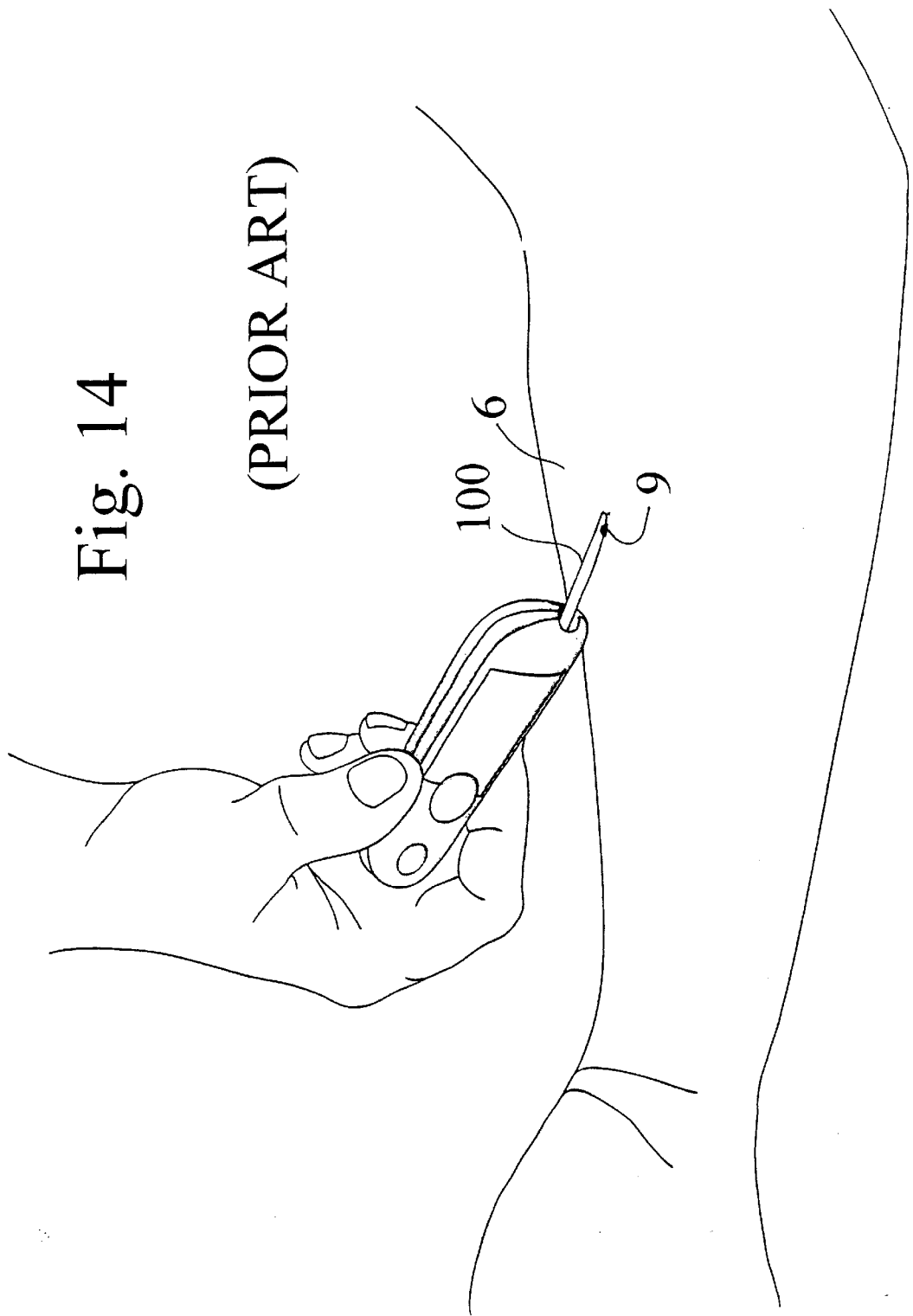
FIG. 14 shows the patient utilizing a prior art glucose sensor strip applied to the blood droplet on the forearm.
Figure 15:
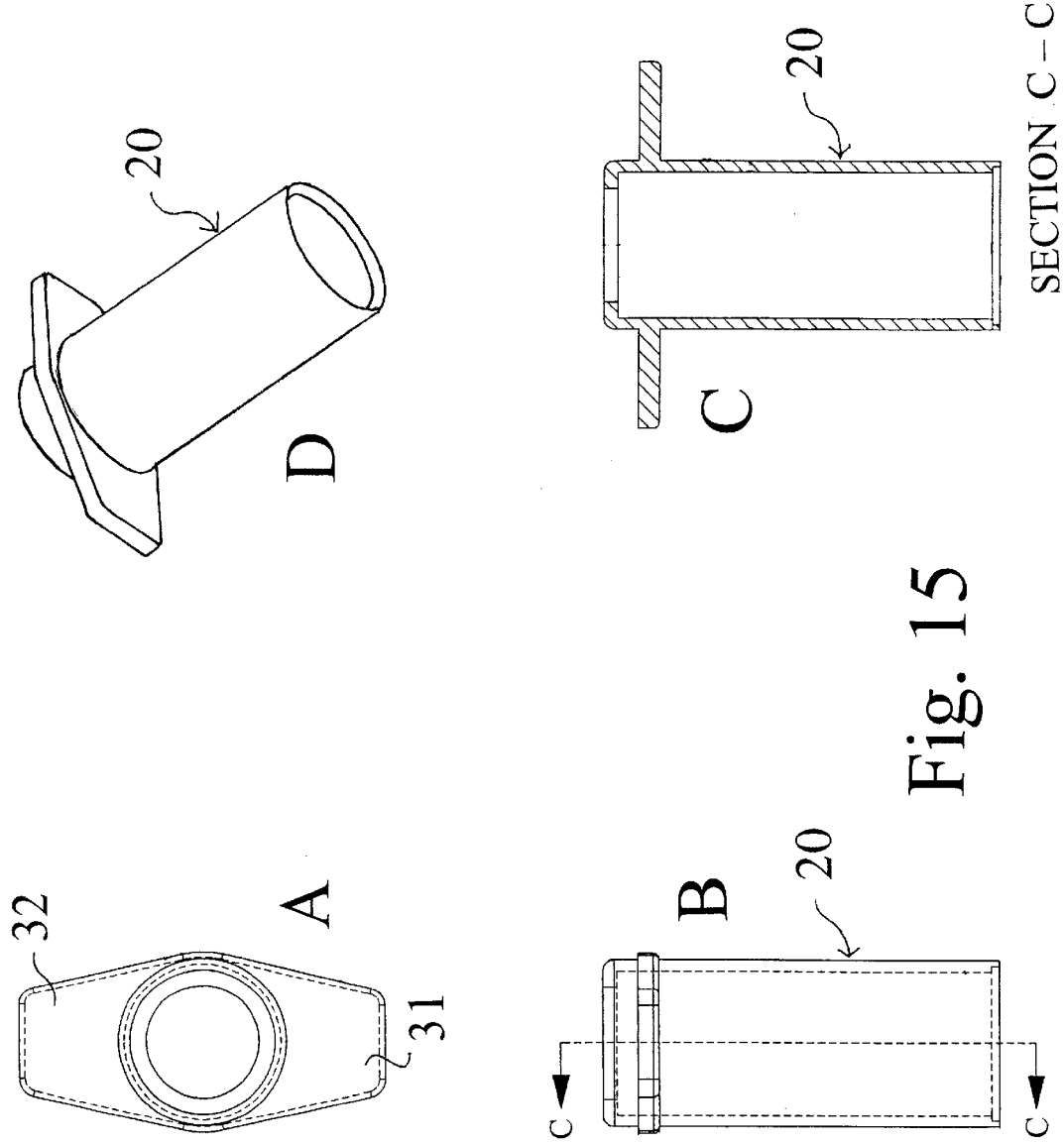
FIGS. 15A–15D are scale drawings showing dimensions of the injection molded cylindrical body.
Figure 16:
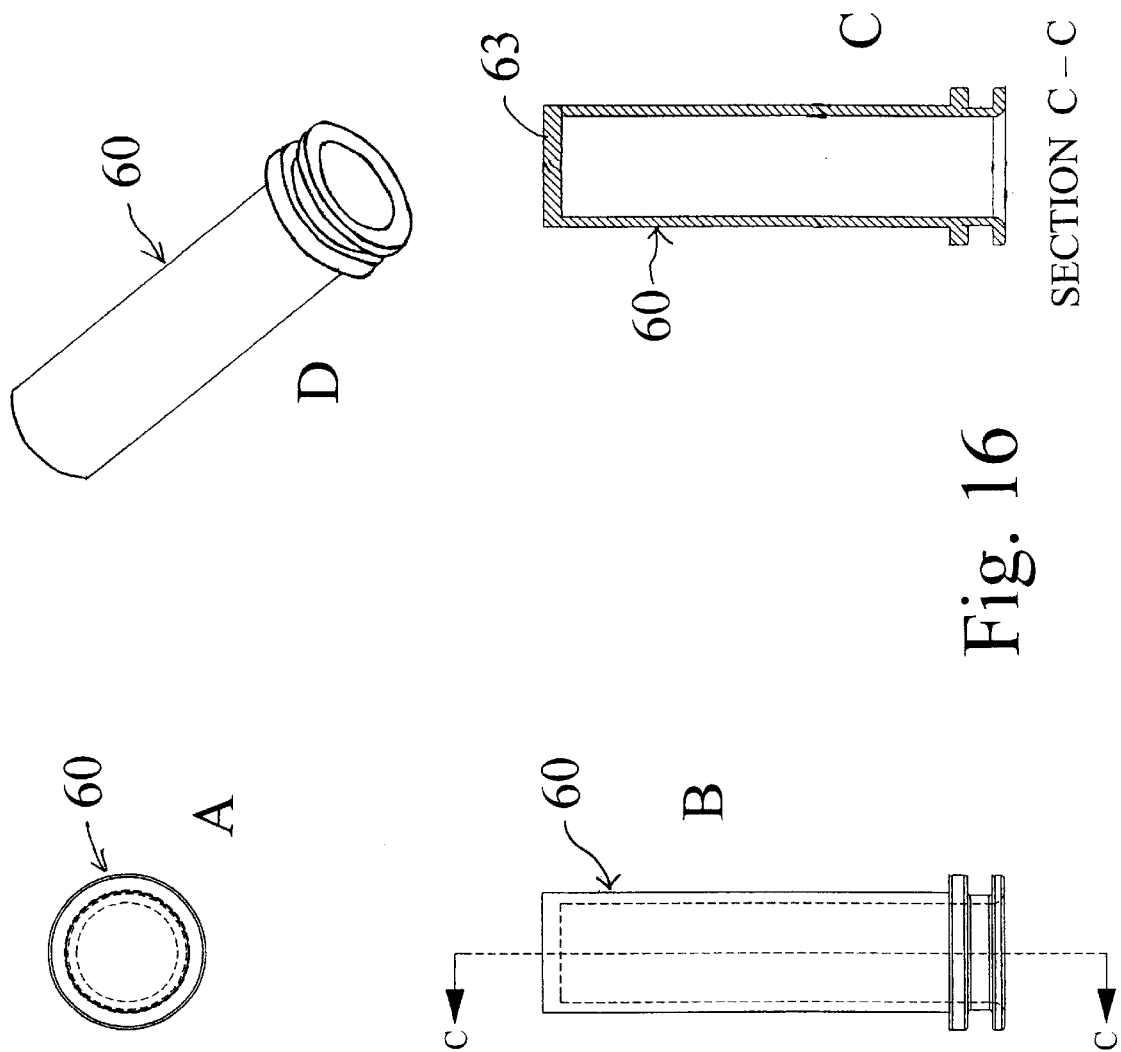
FIGS. 16A–16D are scale drawings showing the injection molded hollow plunger.
Figure 18:
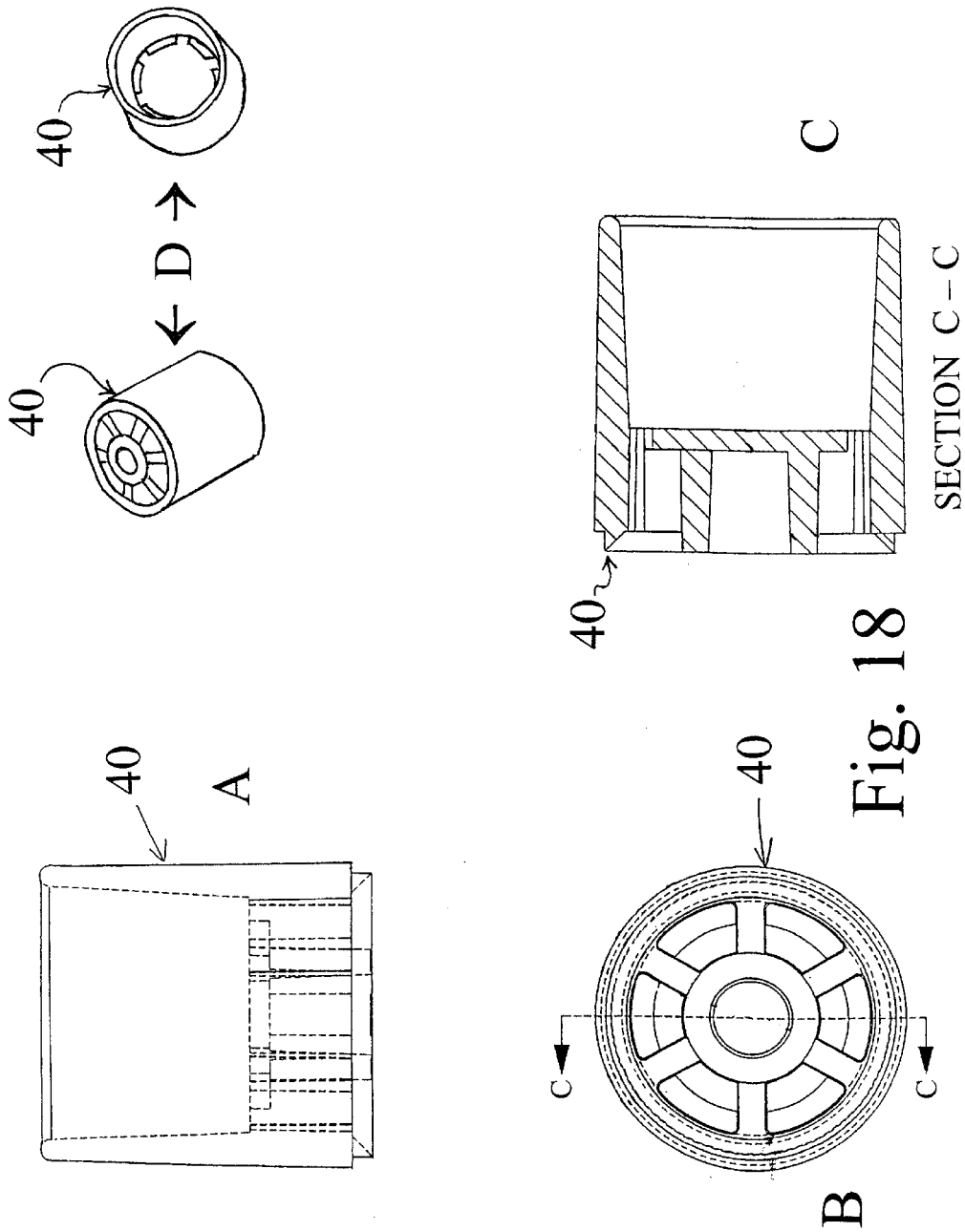
FIGS. 18A–18D are scale drawings showing the transparent plastic injection molded transparent tip.

FIGS. 8–14 illustrate how the present vacuum device 10 is utilized to assist in obtaining a blood sample from a patient's forearm. FIG. 8 shows the patient using a prior art lancet 5 to puncture the skin on the forearm 6. FIGS. 9 and 10 show the user grasping the vacuum device 10 of the present invention and depressing the plunger 60 and holding the plunger 60 down (FIG. 10). Depression of the plunger 60 causes a tension buildup within the spring 90. After the user depresses the plunger, the device 10 is firmly placed against the skin, at the puncture site, as shown in FIG. 11. The plunger is then released resulting in upward movement of the plunger due to spring pressure, as shown in FIG. 12. A partial vacuum is thereby formed within the transparent tip 40 which pulls skin and subcutaneous tissue upward into the chamber. Formation of the enlarging blood drop 9 is easily seen by the user, as shown in FIG. 13. The vacuum is released after the drop has formed by again depressing the plunger. Finally, as shown in FIG. 14, the user places the blood drop 9 onto a prior art glucose sensitive strip 100 to obtain a blood glucose measurement.

FIGS. 2–7 show the separate components of the present invention.

Figure 1:
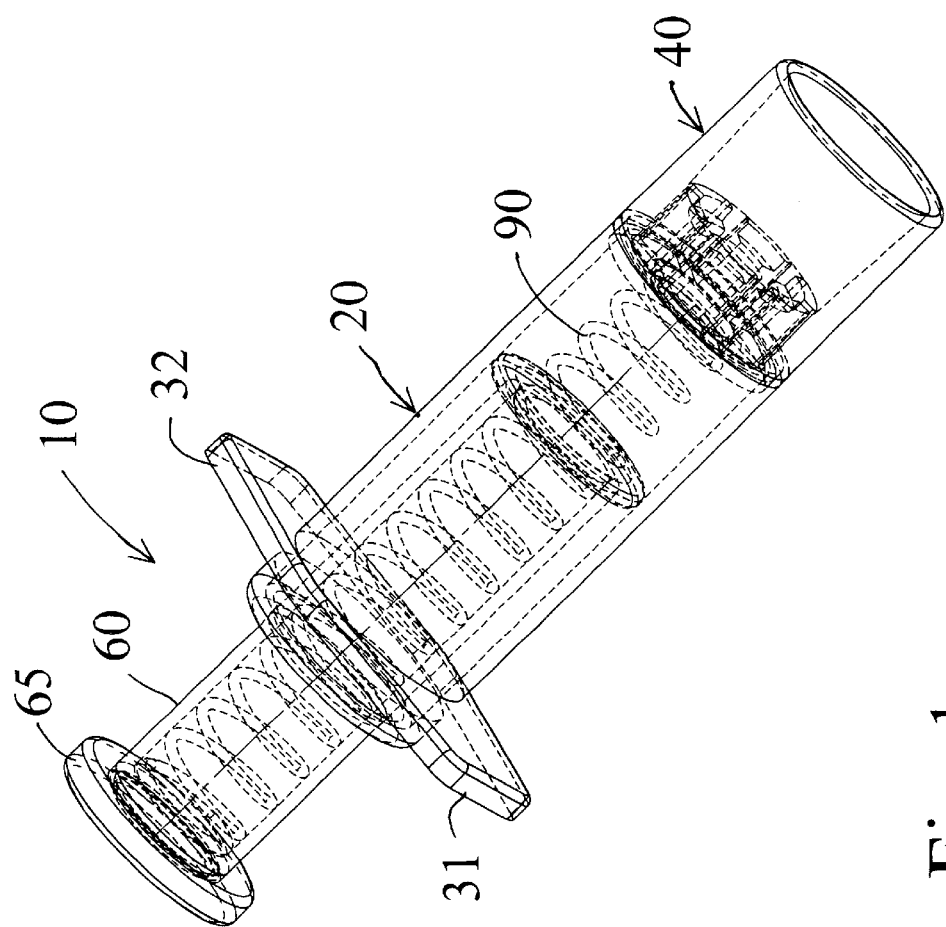
FIG. 1 is a semi-transparent three-dimensional view of the device with the spring inside the plunger and cylindrical body.
Figure 2:
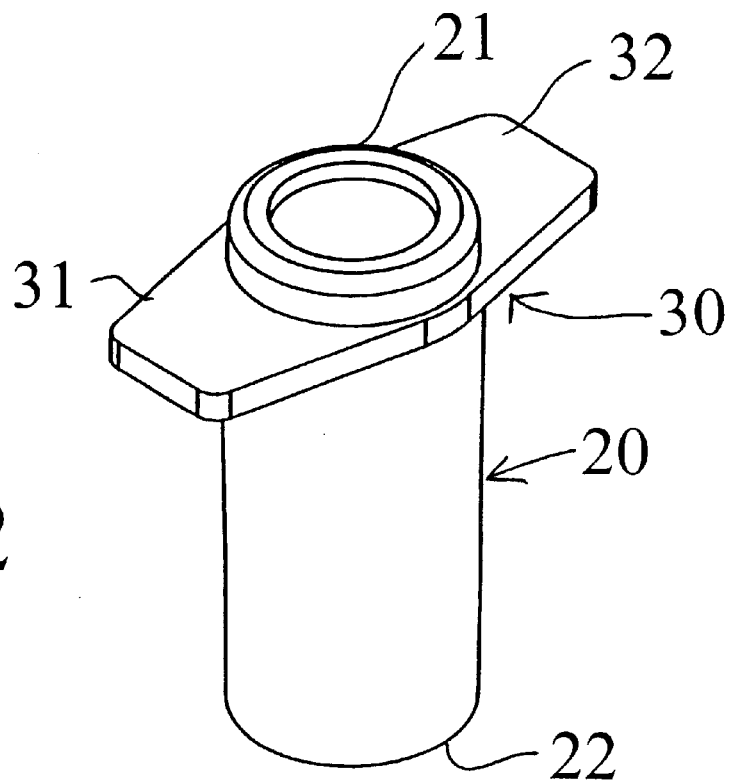
FIG. 2 is a perspective view of the outer cylinder body of the invention with lateral finger flanges.

FIG. 2 shows the hollow body 20 which has an upper end 21 and a lower end 22. The body section 20 is preferably circular in cross section and made of injection molded plastic.

A finger flange means 30 is carried by the hollow body 20 near its upper end 21. Flange means 30 includes in the preferred embodiment two flange members 31 and 32 which may be grasped by two fingers of a user as shown in FIGS. 9–12.

FIG. 3 illustrates in perspective view the transparent tip means 40 which is injection molded. Transparent tip means 40 includes a hollow cylindrical sleeve 41 having a lower end 42. Lower end 42 is intended to contact the user's skin around the preexisting puncture site. The upper end 43 of sleeve 41 is connected to the lower end of cylindrical body 20 by ultrasonic welding. The interior of sleeve 41 carries an integrally molded webbing 50 which includes in the preferred embodiment six separate arms 51–56 which radiate outwardly from the center of sleeve 41 and are molded integrally with the side wall of sleeve 41. Webbing 50 has an annular surface 57 (FIG. 19) formed in arms 51–56 which forms the seat for spring means 90; spring 90 is not shown fully seated against seat 57 in the drawings for clarity. Webbing 50 extends from the top portion of sleeve 41 downwardly through approximately one-third of the height of sleeve 41 as shown best in FIG. 19. Webbing 50 preferably includes an upwardly extending portion 59 having an outer diameter sized to slidably engage the lower portion 91 of spring 90 as shown best in FIG. 19. Webbing 50 not only provides a seat for spring means 90 but also allows air to move freely into and out of the interior of plunger means 60 and simultaneously provides a transparent lower portion 58 shown best in FIG. 19 which allows the user a clear view of the blood droplet 9 as it is forming.

Figure 5:
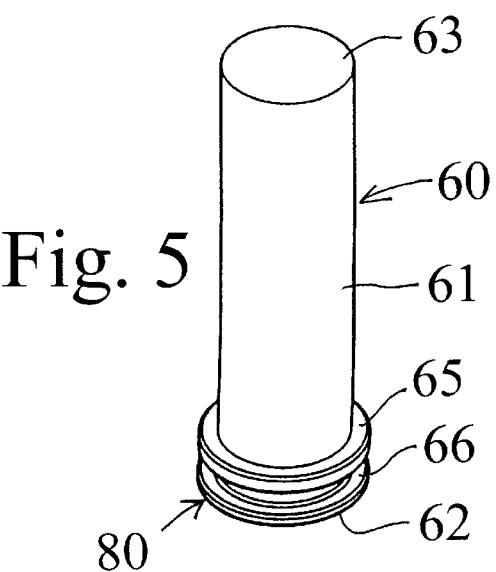
FIG. 5 is a perspective view of the hollow plunger utilized with the present invention and which includes a pair of shoulders which carry therebetween an O ring.
Figure 20:
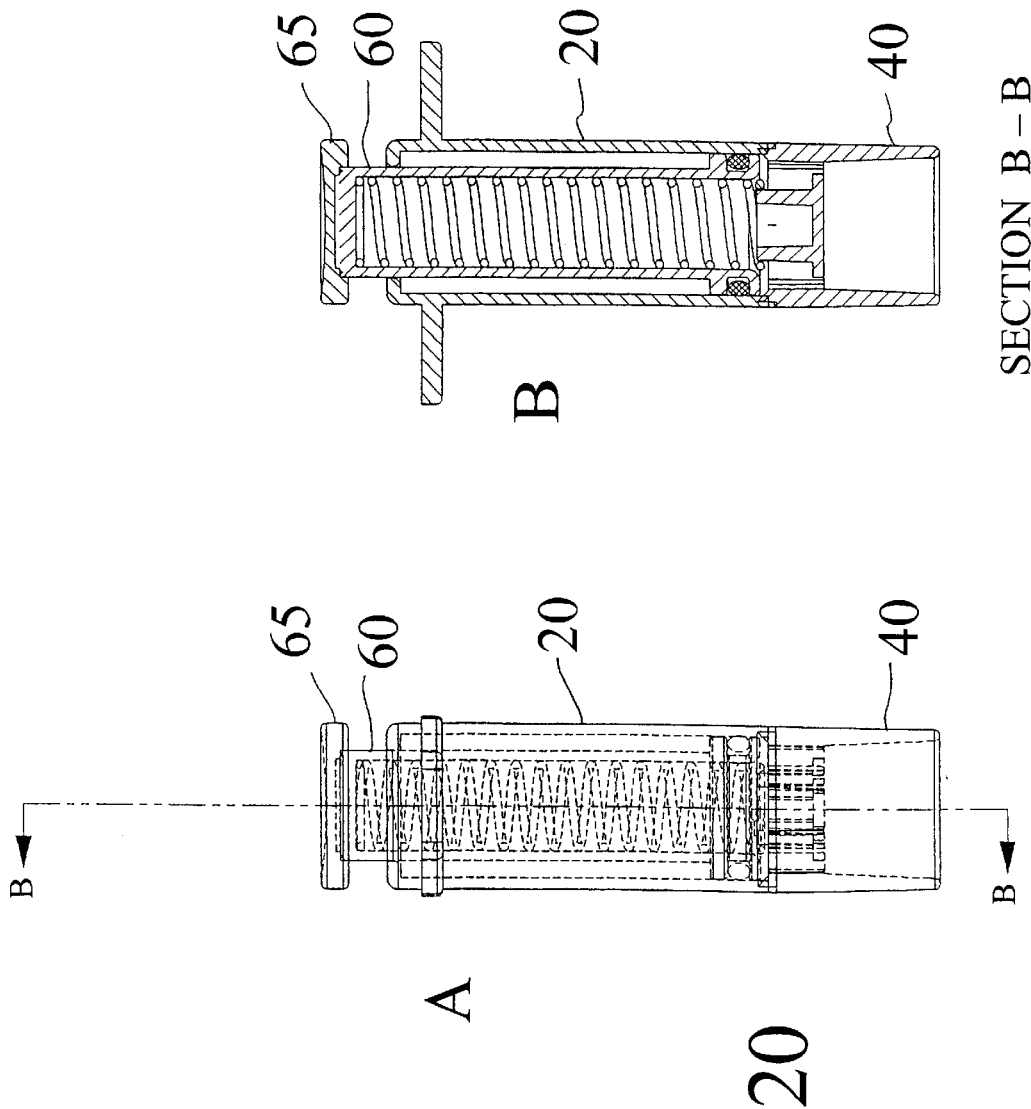
FIGS. 20A and 20B are frontal and sectional views showing the assembled vacuum device with the plunger fully depressed.

FIG. 5 illustrates the hollow plunger means 60 capable of being injection molded. Hollow plunger means 60 includes a cylindrical central sleeve 61 and has a lower end 62 and an upper end 63. Upper end 63 carries an injection molded plunger cap 65 illustrated in FIG. 4 which can be ultrasonically welded to the plunger. Plunger cap 65 has a depressed upper surface 66 designed to comfortably interact with the tip of a user's thumb or finger. The plunger means 60 is movable between a first position illustrated best in FIG. 20 wherein it extends upwardly from hollow body 20 and a second position illustrated best in FIG. 19 wherein it extends downwardly into said hollow body 20. It should be noted that while a solid plunger could be used in a variation of the present invention, a hollow plunger allows the use of the longest possible spring for the best mechanical advantage while at the same time keeping the total length of the device to a minimum.

Figure 6:
FIG. 6 is a perspective view of the O ring used to create a vacuum seal.

FIG. 6 illustrates an O-ring 81 which provides one type of sealing means. Sealing means 80 is provided between the hollow plunger means 60 and hollow body 20 and is illustrated best in FIGS. 19 and 20. The sealing means 80 includes an O-ring 81 (FIG. 6) and a pair of O-ring support shoulders 65 and 66 (FIG. 5) which carry O-ring 81. It is within the scope of the invention to use alternate forms of seal between hollow body 20 and plunger means 60.

Figure 7:
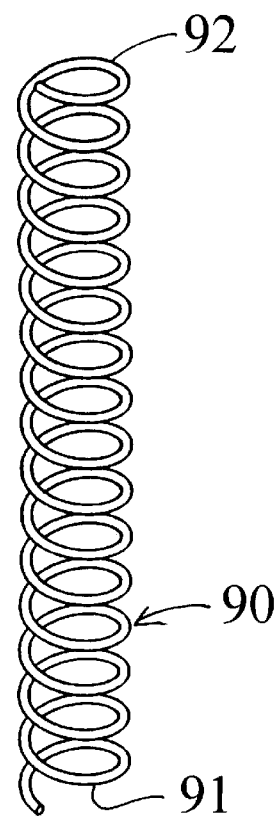
FIG. 7 is a perspective view of a spring which generates a vacuum when allowed to expand.

Spring means 90 is illustrated best in FIG. 7 and is a conventional metallic helical spring having a lower end 91 that seats against webbing 50 and an upper end 92 that seats against the under surface 63 of plunger cap 60. It is also within the scope of the invention to select a wire diameter and coil number for the spring so that the desired vacuum strength is produced over the puncture site.

FIGS. 15 through 18 are self-explanatory scaled parts drawings, illustrating the four key components which are designed to be efficiently injection molded.

What is claimed is:

1. A vacuum device for use in drawing a capillary blood sample from a previously formed puncture site in a patient's skin, comprising:

a hollow body having an upper end and a lower end, plunger means having upper and lower ends and adapted to be slidably carried inside said hollow body, said plunger being movable between a depressed position and an upward position, sealing means between said plunger and said hollow body, said sealing means remaining in sealing contact with said body and plunger as said plunger moves in either direction between its depressed and upward positions, a single spring urging said plunger in an upwardly direction, and a cylindrical tip attached to the lower end of the hollow body and located below said spring, said tip forming a vacuum chamber around said puncture site when the plunger is urged upwardly by said single spring, said single spring, said sealing means and said plunger means cooperating to produce a variable strength vacuum in said vacuum chamber depending on how fully said single spring is compressed by said plunger means, wherein said vacuum device includes only one spring and does not include a lancet for forming a puncture.

2. The apparatus of claim 1 further comprising finger flanges carried by said upper end of said body.

3. The apparatus of claim 1 wherein said plunger means is hollow and said spring means extends through said plunger and seats against a plunger cap.

4. The apparatus of claim 1 wherein the cylindrical tip attached to the lower end of the hollow body is transparent.

5. The apparatus of claim 2 wherein said sealing means comprises an O-ring and an O-ring support carried by the lower end of said plunger and wherein said plunger has a plunger cap and wherein the following four primary components are injection molded plastic:

said hollow body and said finger flanges are formed as a first injection molded part, said cylindrical tip is formed as a second injection molded part, said hollow plunger and said O-ring support is formed as a third injection molded part, and said plunger cap is formed as a fourth injection molded part.

6. A vacuum device actuatable by the thumb and two fingers of one hand for use in drawing a capillary blood sample from a previously formed puncture site, comprising:

a hollow body with an upper end and a lower end, a transparent tip means carried by said lower end of said hollow body, said tip means adapted to contact the user's skin around said puncture site, a finger flange means carried by said hollow body and adapted to be grasped by two of said user's fingers, a hollow plunger means having upper and lower ends and adapted to be slidably carried inside said hollow body, said hollow plunger means having a plunger cap means at its upper end adapted to be depressed by the user's thumb, said plunger means movable between a first position wherein it extends upwardly from said hollow body and a second position wherein it extends downwardly into said hollow body, a sealing means between said hollow plunger means and said hollow body means, said sealing means remaining in sealing contact between said body and plunger means as said plunger moves in either direction between its second and first positions, and a single spring carried inside said hollow body and said hollow plunger means so that said single spring urges said hollow plunger means into said first position, and whereby said user moves said hollow plunger means into said second position by grasping said finger flange means with two fingers and pressing downwardly on said plunger cap means with a thumb, compressing said single spring, and whereby said transparent tip is placed against the skin around said puncture site, and a vacuum is created around said puncture site as the user releases said plunger means and said single spring urges said plunger means towards said first position, wherein the strength of the vacuum is controllable by the user, the vacuum being stronger as said single spring is compressed further by the user, and wherein said vacuum device includes only one spring and does not include a lancet for forming a puncture.

\* \* \* \* \*